United States Patent
Huang et al.

(10) Patent No.: US 9,145,353 B2
(45) Date of Patent: Sep. 29, 2015

(54) METHOD OF PREPARING (S)-2-AMINO-5-METHOXYTETRALIN HYDROCHLORIDE

(75) Inventors: Qingyun Huang, Hefei (CN); Qingguo Huang, Hefei (CN); Meixian Lou, Hefei (CN)

(73) Assignee: Anhui Kelong Institute of Pharmaceutical, Hefei, Anhui (CN)

( * ) Notice: Subject to any disclaimer, the term of this patent is extended or adjusted under 35 U.S.C. 154(b) by 248 days.

(21) Appl. No.: 13/570,210

(22) Filed: Aug. 8, 2012

(65) Prior Publication Data
US 2014/0046095 A1 Feb. 13, 2014

(51) Int. Cl.
C07C 213/02 (2006.01)
C07C 217/74 (2006.01)
C07C 249/02 (2006.01)
C07C 251/20 (2006.01)
C07C 213/08 (2006.01)

(52) U.S. Cl.
CPC ............. C07C 213/02 (2013.01); C07C 213/08 (2013.01); C07C 217/74 (2013.01); C07C 249/02 (2013.01); C07C 251/20 (2013.01); *C07B 2200/07* (2013.01); *C07C 2102/10* (2013.01)

(58) Field of Classification Search
CPC .. C07C 213/02; C07C 217/74; C07C 249/02; C07C 251/20
USPC .................................................. 564/270, 392
See application file for complete search history.

(56) References Cited

U.S. PATENT DOCUMENTS 4,803,227 A * 2/1989 Brandes et al. ............... 514/651

OTHER PUBLICATIONS

Johansson et al., J. Med. Chem. (1985), 28, pp. 1049-1053.*

Hutchins et al., J. Org. Chem. (1983), 48(20), pp. 3412-3422.*

* cited by examiner

*Primary Examiner* — Yong Chu
(74) *Attorney, Agent, or Firm* — Raymond Y. Chan; David and Raymond Patent Firm

(57) ABSTRACT

A method of preparing (S)-2-amino-5-methoxytetralin hydrochloride[(S)-2-amino-5-methoxyl-1,2,3,4-tetrahydronaphthalene hydrochloride], comprising the steps of: (1) producing a compound (I) by addition-elimination reaction of 5-methoxy-2-tetralone and R-(+)-a-phenylethylamine; (2) producing a compound (II) by reduction reaction of the compound (I) with a reducing agent; and (3) producing a compound (II) hydrochloride by reacting the compound (II) with a salt-forming agent, then carrying out reduction reaction with a palladium-carbon catalyst to produce (S)-2-amino-5-methoxytetralin hydrochloride. The method can significantly increase the yield of (S)-2-amino-5-methoxytetralin hydrochloride with short synthetic path, low preparation cost and less pollution, which is environmentally friendly and is suitable for medical industrialized production. The structural formulae of the compound (I) and the compound (II) are:

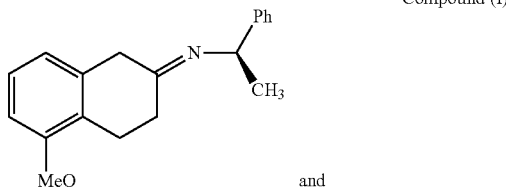

Compound (I)

and

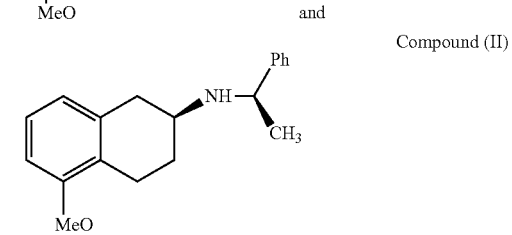

Compound (II)

respectively.

5 Claims, No Drawings

METHOD OF PREPARING (S)-2-AMINO-5-METHOXYTETRALIN HYDROCHLORIDE

BACKGROUND OF THE PRESENT INVENTION

1. Field of Invention

The present invention relates to synthesis of (S)-2-amino-5-methoxytetralin hydrochloride, and more particularly to a synthetic method and a composition of (S)-2-amino-5-methoxytetralin hydrochloride.

2. Description of Related Arts

Parkinson disease (PD) is also known as paralysis agitans which is a slowly progressive movement disorder and is a type of extrapyramidal conditions. Parkinson's disease is a neurodegenerative disease which is common for the middle-aged and the old and the onset age is usually over 60. The symptoms of Parkinson's disease includes tremor or shaking, rigidity or stiff muscles, slow or limited movement, weakness of face muscle and etc. Patients usually cannot handwriting, have difficulty with walking and balance and are easy to fall. In severe cases, patient cannot take care himself or herself and has to lie in bed. As the number of the world's aging population is increased, the number of people suffering from Parkinson's disease is also increased. Parkinson's disease not only imposes a health hazard to the old, but also seriously affects the normal life of the family members of patients.

The pathogenesis of Parkinson's disease is linked to lack of dopamine, which is a central neurotransmitter. Rotigotine is a dopamine receptor agonists and is tested and proved to its ability to significantly improve the condition of a patient and is an effective medication for treatment of Parkinson's disease.

Rotigotine is developed by Schwarz Biosciences for treatment of early-staged secondary Parkinson's disease and late-staged Parkinson's disease, and has a chemical name of (6S)-6-{propyl[2-(2-thienyl)ethyl]amino}-5,6,7,8-tetrahydro-1-naphthalenol. The trade name of Rotigotine is NEUPRO and its structural formula is:

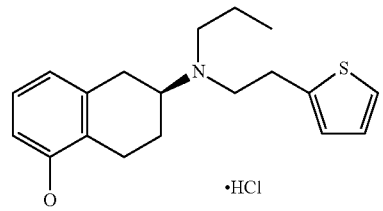 [SMILES: CCCN(CCc1cccs1)[C@H]1CCc2c(O)cccc2C1 ; Cl]

At present, the synthesis of Rotigotine generally utilizes (S)-2-amino-5-methoxyl-1,2,3,4-tetrahydronaphthalene as the raw material, and the synthesis of (S)-2-amino-5-methoxyl-1,2,3,4-tetrahydronaphthalene mainly include benzylamination or methoxylamination. The two synthetic paths are illustrated as follows:

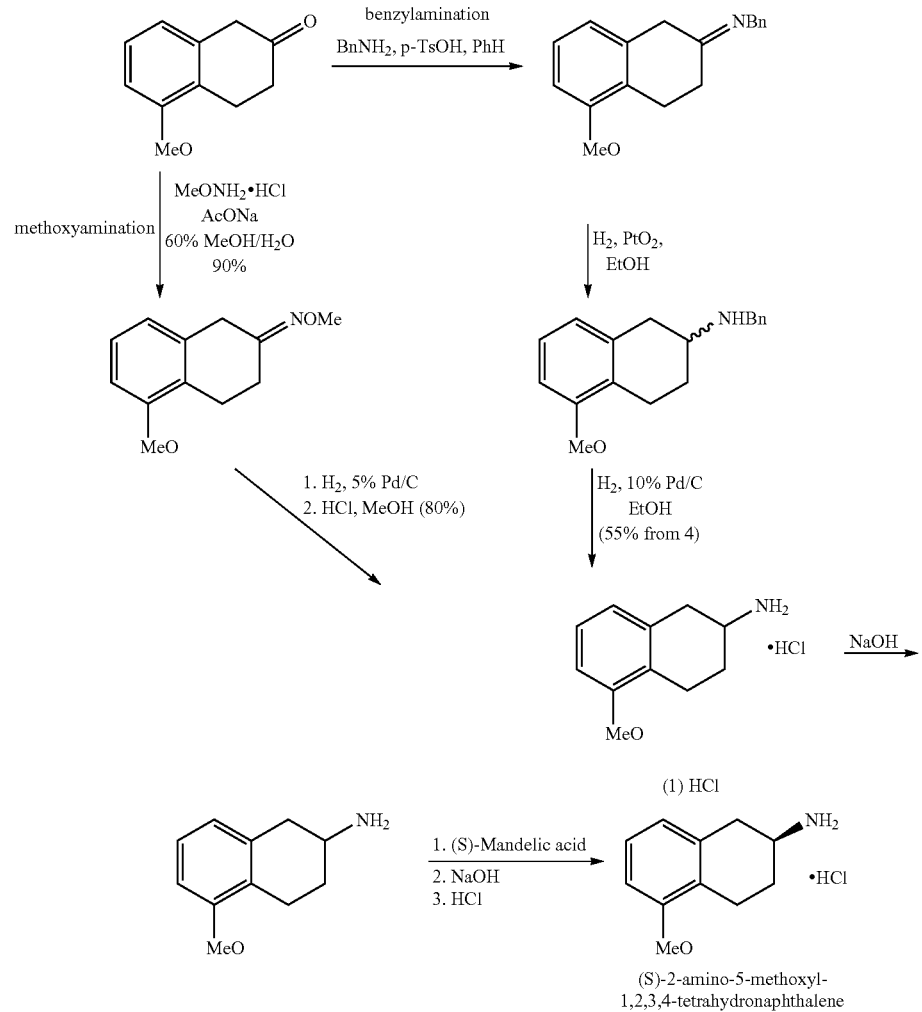

The two methods as shown above utilize 5-methoxy-2-tetraone as the starting material to produce (R)-2-amino-5-methoxytetralin. Then, (S)-Mandelic acid is used to resolve the desire enantiomer to obtain (S)-2-amino-5-methoxytetralin. However, the yield of the final desired product by chiral resolution is very low in which the yield by benzylamination (which refers to reaction with benzylamine) is only 17% and the yield by methoxyamination (which refers to reaction with methoxyamine) is only 23.5%. Therefore the use of these two methods in pharmaceutical industry is greatly limited.

SUMMARY OF THE PRESENT INVENTION

Accordingly, an object of the present invention is to provide a synthetic method of (S)-2-amino-5-methoxytetralin which can greatly increase the yield of the final product of (S)-2-amino-5-methoxytetralin hydrochloride.

Additional advantages and features of the invention will become apparent from the description which follows, and may be realized by means of the instrumentalities and combinations particular point out in the appended claims.

According to the present invention, the foregoing and other objects and advantages are attained by a synthetic method of (S)-2-amino-5-methoxytetralin which comprises the steps of:

(1) producing a compound (I) by addition-elimination reaction of 5-methoxy-2-tetralone and R-(+)-a-phenylethylamine;

(2) producing a compound (II) by reduction reaction of the compound (I) with a reducing agent; and (3) producing a compound (II) hydrochloride by reacting the compound (II) with a salt-forming agent, then carrying out reduction reaction with a palladium-carbon catalyst to produce (S)-2-amino-5-methoxytetralin hydrochloride, where the compound (I) and compound (II) have the following structural formulae:

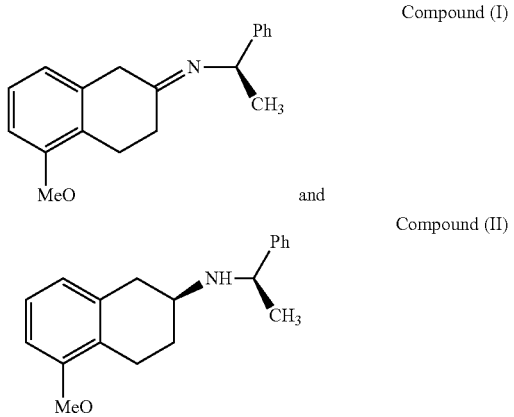

respectively.

Conventional method employs benzylamination or methoxyamination and makes use of racemic resolution to obtain (S)-2-amino-5-methoxytetralin hydrochloride. However, this synthetic process has a very low yield of (S)-2-amino-5-methoxytetralin hydrochloride. Accordingly, the present invention utilizes asymmetric induction in the chiral synthesis process to produce (S)-2-amino-5-methoxytetralin hydrochloride such that the problem of low yield due to racemic resolution is resolved.

The formation mechanism of configuration of the present invention includes the steps of carrying out addition-elimination reaction of non-chiral substrate (which is 5-methoxy-2-tetralone) and chiral reagent (which is R-(+)-a-phenylethylamine) to produce a chiral product (which is compound I); then utilizing compound (I) for asymmetric induction; and constructing the bonding structure between cyclohexane and NH with a reducing agent to produce the compound (II).

In the addition-elimination reaction, under the effect of catalyst, the two hydrogen of the amino group in R-(+)-a-phenylethylamine attack the carbon atom and the oxygen atom in the carbonyl group of 5-methoxy-2-tetralone such that a hydroxyl group is formed by addition reaction. Since the hydroxyl group is very unstable under this condition, an elimination reaction will occurred instantaneously in which $H_2O$ is removed and a double bond is formed to bond with the nitrogen atom of R-(+)-a-phenylethylamine such that compound I is formed. According to the rule of nomenclature, the chemical name of compound I is: N—(R)-phenylethyl-5-methoxy-1,2,3,4-tetralin-2-imine and the reaction is illustrated as follows:

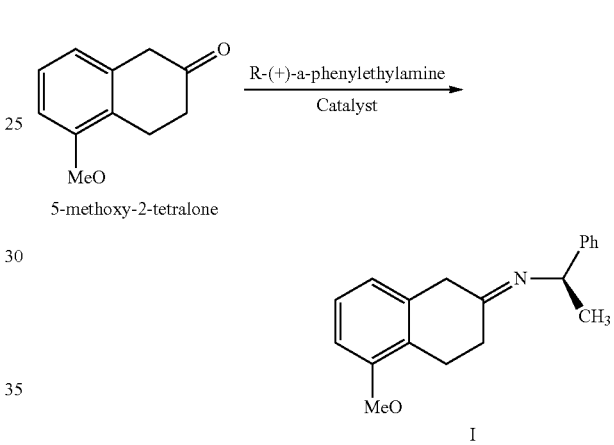

In particular, a molar ratio of 5-methoxy-2-tetralone and R-(+)-a-phenylethylamine is 1:0.5~5, and preferably, the molar ratio of 5-methoxy-2-tetralone and R-(+)-a-phenylethylamine is 1:2. The catalyst used in the addition-elimination reaction is selected from $C_1$-$C_4$ alkyl carboxylic acid, $C_1$-$C_4$ alkyl sulfonate, $C_1$-$C_4$ arcyl sulfonic acid, hydrochloric acid, sulfuric acid, nitric acid, phosphoric acid, dihydrogen phosphate, isopropyl titanate, ethyl titanate and tetrabutyl titanate. Preferably, the catalyst is selected from methanesulfonic acid, p-toluenesulfonic acid, sulfuric acid and isopropyl titanate. The solvent used in the addition-elimination reaction is selected from one or more from the group consisting of benzene, toluene, xylene, halobenzene, nitrobenzene, ethyl benzene, ethyl acetate, methyl acetate, butyl acetate, propyl acetate, ethyl ether, propyl ether, butyl ether, methyl tert-butyl ether, tetrahydrofuran, dioxane, 2-methyl tetrahydrofuran, 1,2-dichloroethane, dichloromethane and chloroform. Preferably, the solvent is one, two or more of toluene, butyl acetate and methyl tert-butyl ether.

In the reduction reaction, compound I is reduced under the reaction of reducing agent, and the configuration of the bonding structure between cyclohexane and NH is complete by asymmetric induction between molecules of the compound I such that compound II is produced. According to the rule of nomenclature, the chemical name of compound II is: N—[(R)-1-phenylethyl]-2-amino-5-methoxy-1,2,3,4-tetralin and the reaction is illustrated as follows:

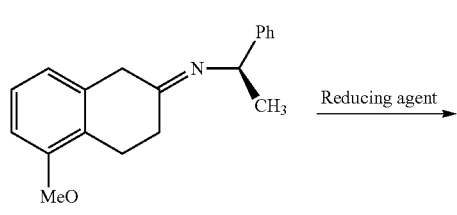

I

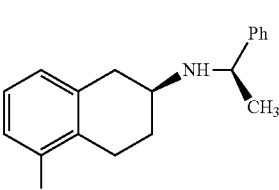

II

In particular, the molar ratio of compound I and reducing agent is 1:0.55. Preferably, the molar ratio of compound I and reducing agent is 1:2. The reaction temperature is −80° C.~50° C., and is preferably −30° C.~20° C. The reducing agent is preferably selected from NaBH$_4$, KBH$_4$, LiBH$_4$ and Zn(BH$_4$)$_2$. The solvent for reduction reaction in this step is selected from one, two or more from the group consisting of C$_1$-C$_4$ alkyl alcohol, ethyl ether, propyl ether, butyl ether, methyl tert-butyl ether, tetrahydrofuran, dioxane, 2-methyl tetrahydrofuran, water, benzene, toluene, halobenzene, nitrobenzene, xylene, 1,2-dichloroethane, dichloromethane and chloroform. Preferably, the solvent is one, two or more of tetrahydrofuran, ethanol and methanol.

In the step (3) of the present invention, compound II is reacted with salt-forming agent to form a compound II salt, then a catalytic reaction with palladium-carbon catalyst and hydrogen gas is carried out to break the bonding between the NH and the CH which connects to the benzene ring while adding a hydrogen by reduction to produce (S)-2-amino-5-methoxytetralin hydrochloride and the reaction is illustrated as follows:

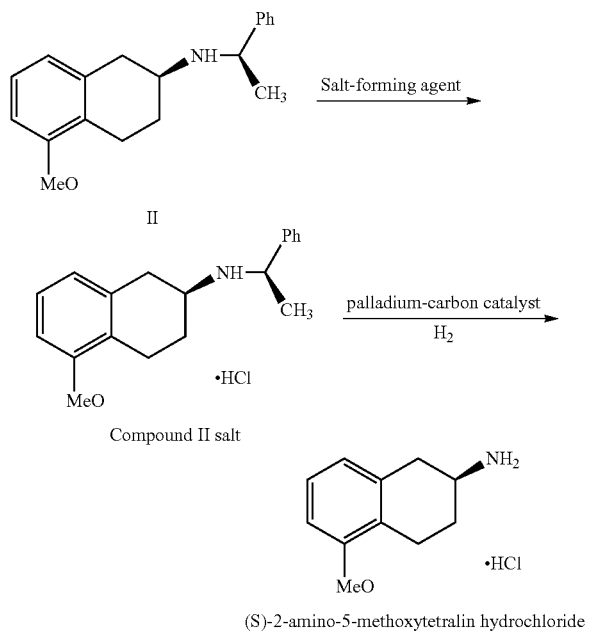

In particular, the salt-forming agent is ethyl ether-HCl or ethyl acetate-HCl. The palladium-carbon catalyst is preferably Pd/C or Pd(OH)$_2$C. The reaction temperature is 20° C.~200° C. and is preferably 50° C.~120° C. The solvent is selected from one, two or more from the group consisting of C$_1$-C$_4$ alkyl alcohol, ethyl ether, propyl ether, butyl ether, methyl tert-butyl ether, tetrahydrofuran, dioxane, 2-methyl tetrahydrofuran, water, benzene, toluene, halobenzene, nitrobenzene, xylene, 1,2-dichloroethane, dichloromethane and chloroform. Preferably, the solvent is one, two or more of tetrahydrofuran, ethanol and methanol.

The present invention employs asymmetric induction for the synthesis of (S)-2-amino-5-methoxytetralin hydrochloride such that the yield achieved is about 68.7%, the purity is 99%, the enantiomeric excess (the optical purity) is 99.9%.

In accordance with another aspect of the invention, the present invention provides a composition having the structural formula of compound I as follows:

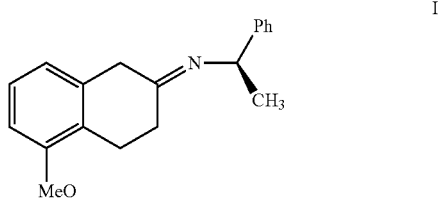 [SMILES: COc1cccc2c1CC/C(=N\[C@H](C)c1ccccc1)C2]

I

According to the preferred embodiment of the present invention, compound I is prepared by addition-elimination reaction of 5-methoxy-2-tetralone and R-(+)-a-phenylethylamine under the catalytic reaction of a catalyst, and the reaction is illustrated as follows:

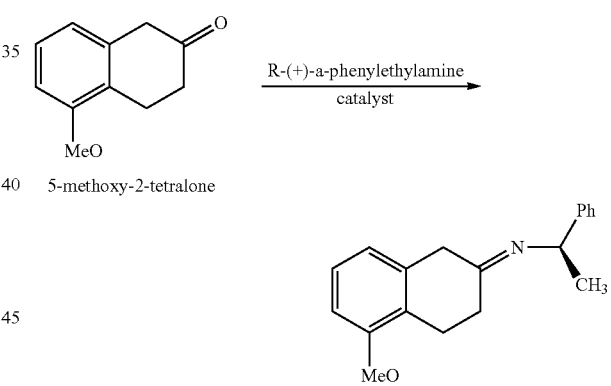

5-methoxy-2-tetralone

The molar ratio of 5-methoxy-2-tetralone and R-(+)-a-phenylethylamine is 1:0.5~5, and preferably, the molar ratio of 5-methoxy-2-tetralone and R-(+)-a-phenylethylamine is 1:2. The catalyst used in the addition-elimination reaction is selected from C$_1$-C$_4$ alkyl carboxylic acid, C$_1$-C$_4$ alkyl sulfonate, C$_1$-C$_4$ arcyl sulfonic acid, hydrochloric acid, sulfuric acid, nitric acid, phosphoric acid, dihydrogen phosphate, isopropyl titanate, ethyl titanate and tetrabutyl titanate. Preferably, the catalyst is selected from methanesulfonic acid, p-toluenesulfonic acid, sulfuric acid and isopropyl titanate. The solvent used in the addition-elimination reaction is selected from one or more from the group consisting of benzene, toluene, xylene, halobenzene, nitrobenzene, ethyl benzene, ethyl acetate, methyl acetate, butyl acetate, propyl acetate, ethyl ether, propyl ether, butyl ether, methyl tert-butyl ether, tetrahydrofuran, dioxane, 2-methyl tetrahydrofuran, 1,2-dichloroethane, dichloromethane and chloroform. Preferably, the solvent is one, two or more of toluene, butyl acetate and methyl tert-butyl ether.

According to the preferred embodiment of the present invention, the compound I can be used for the synthesis of (S)-2-amino-5-methoxytetralin hydrochloride. In the synthesis of (S)-2-amino-5-methoxytetralin hydrochloride, the compound I is reacted with a reducing agent to carry out a reduction reaction to produce a compound II. Then the compound II is reacted with a salt-forming agent to produce a compound II salt. The compound II salt is then reduced by hydrogen gas with palladium-carbon catalyst to produce (S)-2-amino-5-methoxytetralin hydrochloride. The reaction is illustrated as follows:

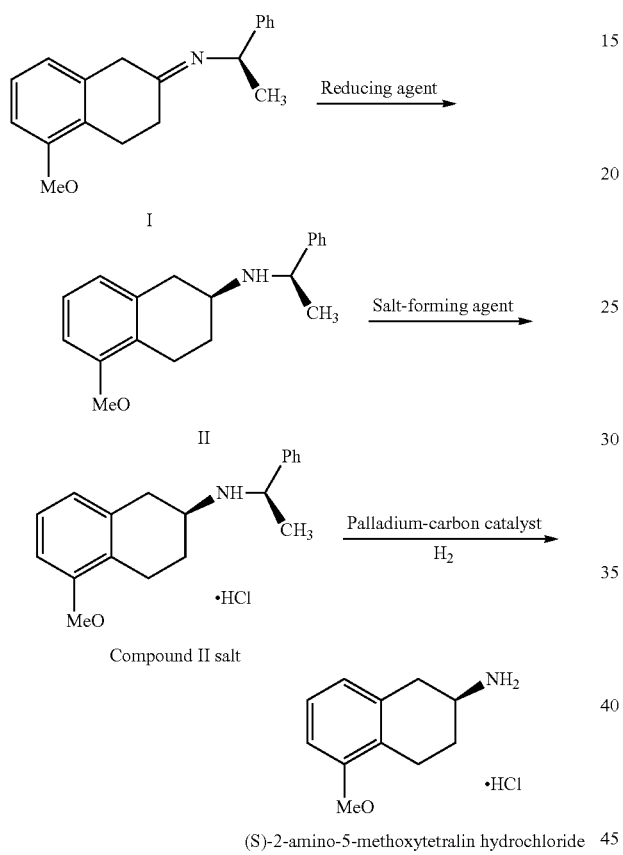

In particular, the salt-forming agent is ethyl ether-HCl or ethyl acetate-HCl. The palladium-carbon catalyst is preferably Pd/C or Pd(OH)$_2$C. The molar ratio of compound I and reducing agent is 1:0.5~5. Preferably, the molar ratio of compound I and reducing agent is 1:2. In the reaction which produce compound II from compound I, the reaction temperature is −80° C.~50° C., and is preferably −30° C.~20° C. In the reaction which produce (S)-2-amino-5-methoxytetralin hydrochloride from compound II salt, the reaction temperature is 20° C.~200° C. and is preferably 50° C.~120° C. The reducing agent is preferably selected from NaBH$_4$, KBH$_4$, LiBH$_4$ and Zn(BH$_4$)$_2$.

The solvent is selected from one, two or more from the group consisting of C$_1$-C$_4$ alkyl alcohol, ethyl ether, propyl ether, butyl ether, methyl tert-butyl ether, tetrahydrofuran, dioxane. 2-methyl tetrahydrofuran, water, benzene, toluene, halobenzene, nitrobenzene, xylene, 1,2-di chloroethane, dichloromethane and chloroform. Preferably, the solvent is one, two or more of tetrahydrofuran, ethanol, water and methanol.

In accordance with another aspect of the invention, the present invention provides a composition having the structural formula of compound II as follows:

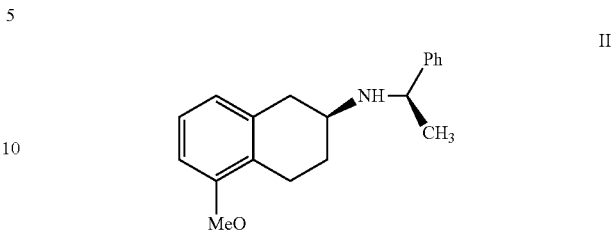

In the preparation of compound II, a compound I is first produced by addition-elimination reaction of 5-methoxy-2-tetralone and R-(+)-a-phenylethylamine. The compound I then reacts with reducing agent for reduction reaction to produce compound II. The reaction is illustrated as follows:

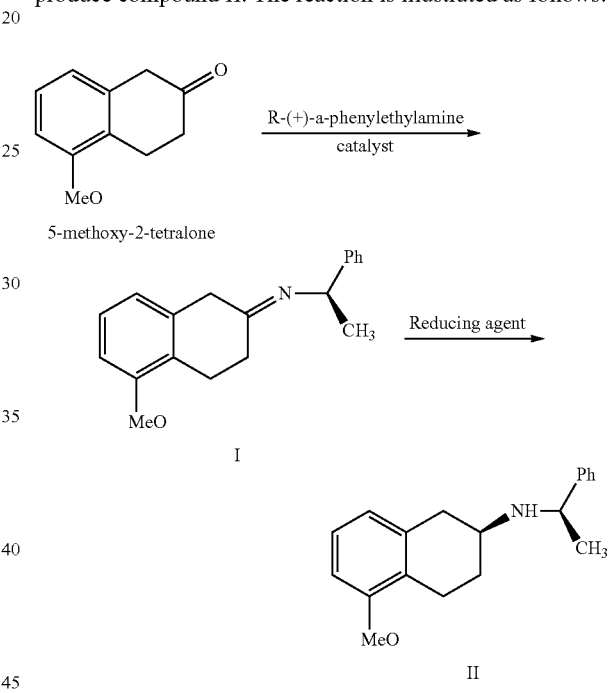

The molar ratio of 5-methoxy-2-tetralone and R-(+)-a-phenylethylamine is 1:0.5~5, and is preferably 1:2. The catalyst used in the addition-elimination reaction is selected from C$_1$-C$_4$ alkyl carboxylic acid, C$_1$-C$_4$ alkyl sulfonate, arcyl sulfonic acid, hydrochloric acid, sulfuric acid, nitric acid, phosphoric acid, dihydrogen phosphate, isopropyl titanate, ethyl titanate and tetrabutyl titanate, and is preferably selected from methanesulfonic acid, p-toluenesulfonic acid, sulfuric acid and isopropyl titanate. The solvent used in the addition-elimination reaction is selected from one or more from the group consisting of benzene, toluene, xylene, halobenzene, nitrobenzene, ethyl benzene, ethyl acetate, methyl acetate, butyl acetate, propyl acetate, ethyl ether, propyl ether, butyl ether, methyl tert-butyl ether, tetrahydrofuran, dioxane, 2-methyl tetrahydrofuran, 1,2-dichloroethane, dichloromethane and chloroform. Preferably, the solvent is one, two or more of toluene, butyl acetate and methyl tert-butyl ether.

The molar ratio of compound I and reducing agent is 1:0.5~5. Preferably, the molar ratio of compound I and reducing agent is 1:2. The reducing agent is preferably selected from NaBH$_4$, KBH$_4$, LiBH$_4$ and Zn(BH$_4$)$_2$. The reaction temperature is −80° C.~50° C., and is preferably −30° C.~20° C. The solvent for reduction reaction in this step is selected from one, two or more from the group consisting of $C_1$-$C_4$ alkyl alcohol, ethyl ether, propyl ether, butyl ether, methyl tert-butyl ether, tetrahydrofuran, dioxane, 2-methyl tetrahydrofuran, water, benzene, toluene, halobenzene, nitrobenzene, xylene, 1,2-dichloroethane, dichloromethane and chloroform. Preferably, the solvent is one, two or more of tetrahydrofuran, ethanol and methanol.

According to the preferred embodiment of the present invention, the compound II can also be used for the synthesis of (S)-2-amino-5-methoxytetralin hydrochloride. In the synthesis of (S)-2-amino-5-methoxytetralin hydrochloride, the compound II is reacted with a salt-forming agent to produce a compound II salt. The compound II salt is then reduced by hydrogen gas with palladium-carbon catalyst to produce (S)-2-amino-5-methoxytetralin hydrochloride. The reaction is illustrated as follows:

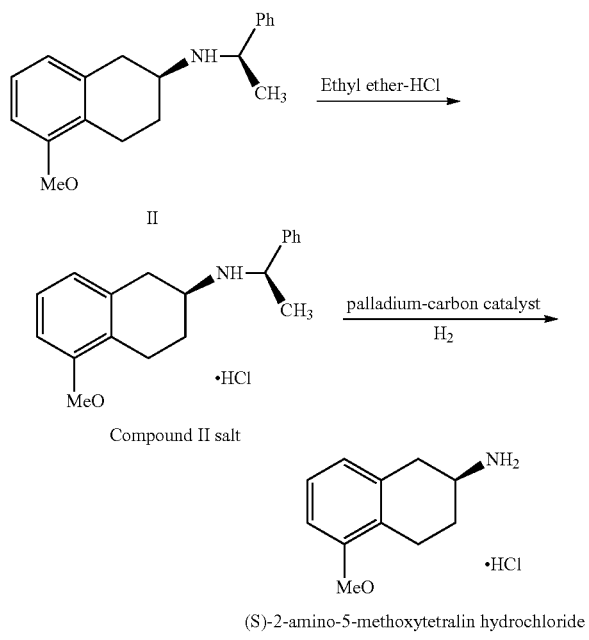

The salt-forming agent is ethyl ether-HCl or ethyl acetate-HCl. The palladium-carbon catalyst is preferably Pd/C or Pd(OH)$_2$C. In the synthesis of (S)-2-amino-5-methoxytetralin hydrochloride from compound II salt, the reaction temperature is 20° C.~200° C. and is preferably 50° C.~120° C. The solvent used in this step is selected from one, two or more from the group consisting of $C_1$-$C_4$ alkyl alcohol, ethyl ether, propyl ether, butyl ether, methyl tert-butyl ether, tetrahydrofuran, dioxane, 2-methyl tetrahydrofuran, water, benzene, toluene, halobenzene, nitrobenzene, xylene, 1,2-dichloroethane, dichloromethane and chloroform. Preferably, the solvent is one, two or more of tetrahydrofuran, ethanol, water and methanol.

Accordingly, in view of the above technical features of the present invention, the present invention can significantly increase the yield of (S)-2-amino-5-methoxytetralin hydrochloride with short synthetic path, low preparation cost and less pollution, which is environmentally friendly and is suitable for medical industrialized production.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

According to the preferred embodiment of the present invention, the present invention provides a synthesis method of (S)-2-amino-5-methoxytetralin hydrochloride and compounds for the synthesis of (S)-2-amino-5-methoxytetralin hydrochloride. The person skilled in the art will understand the present invention through the disclosure of the present invention and all modifications such as changes of reaction parameters and conditions encompassed within the spirit and scope of the disclosure of the present invention are included in the present invention. It is worth mentioning that any changes or substitution made by the skilled in the art which is obvious to the skilled in the art is are encompassed within the spirit and scope of the disclosure of the present invention and are included in the present invention. It will thus be seen that the objects of the present invention have been fully and effectively accomplished. It embodiments have been shown and described for the purposes of illustrating the functional and structural principles of the present invention and is subject to change without departure from such principles.

The present invention is further illustrated as follows:

Embodiment 1

A Process of Making (S)-2-Amino-5-Methoxytetralin Hydrochloride According to the Preferred Embodiment of the Present Invention 1. Synthesis of Compound I Add 72 g (409 mMol) of 5-methoxy-2-tetralone, 62 g (512 mMol) of R-(+)-a-phenylethylamine, 3.2 g of p-toluenesulfonic acid and 2500 ml of toluene into a 5 L reaction flask which is opened to manifold; under the protection of nitrogen atmosphere, stir and heat until the reflux reaction is complete. Then concentrate the reaction liquid under vacuum to obtain an oily liquid of compound I. The reaction is illustrated as follows:

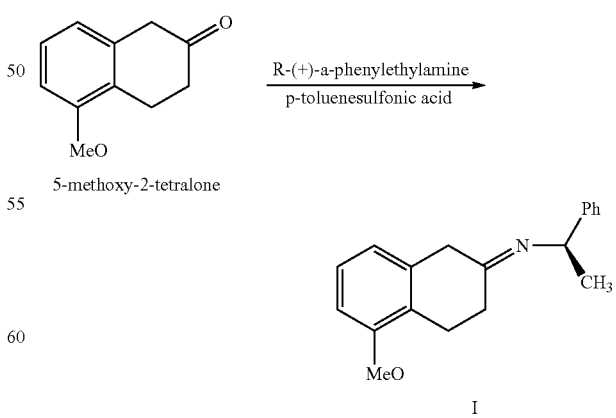

The oily liquid is analyzed by NMR spectroscopy and is determined to have a structural formula consistent to the compound I.

2. Synthesis of Compound II

Add 125 g (409 mMol) of compound I obtained from the above method and 1500 mL anhydrous ethanol into a 2 L four-necked flask; stir until the temperature of the reacting mixture is decreased to reach −20° C.~−10° C.; and then start adding 24 g (631 mMol) of sodium tetrahydridoborate slowly and allow reaction at −20° C.~−10° C. until the reaction is complete. Adjust pH to about 7 by 10% hydrochloric acid. Concentrate and drying the reactants and then add 400 mL of water and 100 mL ethyl acetate. While stirring, adjust pH to about 10 by 10% sodium hydroxide solution and allow settling for stratification. Then the water layer is extracted by 1000 mL of ethyl acetate. Mixing the organic layer obtained from the above two extraction process. Wash twice with 400 mL and 200 mL water respectively. Dry by anhydrous $Na_2SO_4$. Filter and concentrate to obtain 126 g of oily liquid, which is compound II. The reaction is illustrated as follows:

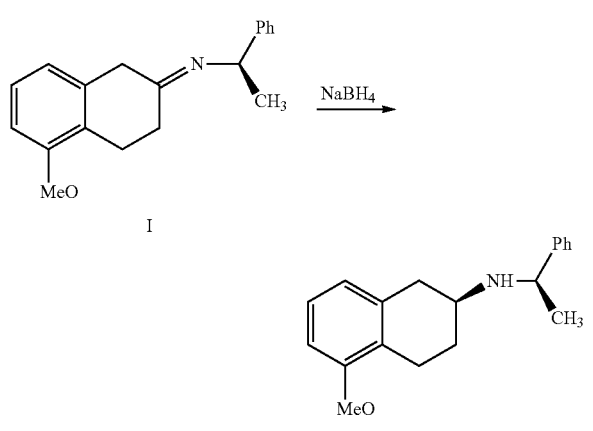

The oily liquid is analyzed by NMR spectroscopy and is determined to have a structural formula consistent to that of the compound II. The results are shown as follows:

$^1$H-NMR ($CDCl_3$, δ (ppm)): 2.02 (1H), 2.12-2.18 (3H), 2.28 (1H), 2.32-2.42 (2H), 2.95-3.02 (2H), 3.38-3.42 (2H), 3.74 (3H), 4.50-4.52 (1H), 6.53-6.61 (2H), 6.98-7.03 (1H), 7.25 (1H), 7.32-7.44 (2H), 7.69-7.71 (2H).

3. Synthesis of (S)-2-amino-5-methoxytetralin hydrochloride

Dilute 126 g of compound II obtained from the above process with 200 mL ethyl acetate. Then add 500 mL ethyl acetate-HCl solution. Obtain a solid by precipitation. Filter and vacuum drying to obtain 100 g of a generally white solid, which is compound II salt.

Add 100 g (404 mMol) of compound II salt, 2300 mL anhydrous ethanol, 80 mL water and 18 g $Pd(OH_2)/C$ into a 5 L four-necked flask. Introduce nitrogen gas into the flask for 30 minutes. Then, introduce $H_2$ while increasing temperature to 25° C.~35° C. and allow reaction. After the reaction is complete, stop the supply of $H_2$. Filter to obtain a filtrate. Concentrate and dry the filtrate. Add 1000 mL ethyl acetate to the residue, reflux for 30 min, cooling and allow crystallization. Filter, dry and vacuum drying to obtain 60 g of a generally white solid, which is (S)-2-amino-5-methoxytetralin hydrochloride. Based on the quantity of 5-methoxy-2-tetralone, the overall yield is 68.7%, the purity is greater than 99% and the enantiomeric excess is 98.5%. If this generally white solid is further refined once, the refining yield is 93%, the overall yield is 63.9%, the purity is greater than 99.5% and the enantiomeric excess is 99.9%. The reaction is illustrated as follows:

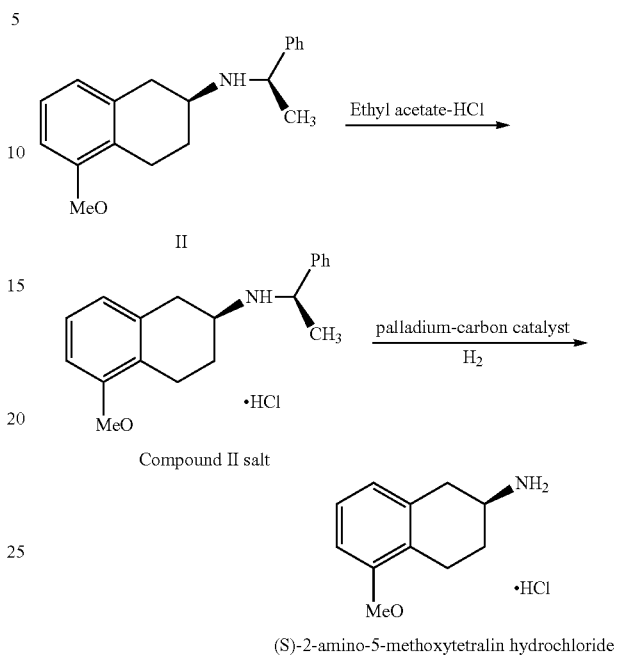

The generally white solid is analyzed by NMR spectroscopy and is determined to have a structural formula consistent to that of the (S)-2-amino-5-methoxytetralin hydrochloride. The results are shown as follows:

$^1$H-NMR ($D_2O$, δ (ppm)): 1.75-1.80 (1H), 2.14-2.17 (1H), 2.52-2.63 (1H), 2.75-2.87 (2H), 3.06-3.13 (1H). 3.45-3.56 (1H), 3.75 (3H), 6.74-6.83 (21-1), 7.12-7.17 (1H).

Embodiment 2

A Process of Making (S)-2-Amino-5-Methoxytetralin Hydrochloride According to the Preferred Embodiment of the Present Invention

1. Synthesis of Compound I

Add 72 g (409 mMol) of 5-methoxy-2-tetralone, 62 g (512 mMol) of R-(+)-a-phenylethylamine, 3.2 g of methanesulfonate and 3000 ml of ethyl acetate into a 5 L reaction flask which is opened to manifold; under the protection of nitrogen atmosphere, stir and heat until the reflux reaction is complete. Then concentrate the reaction liquid under vacuum to obtain an oily liquid of compound I. The reaction is illustrated as follows:

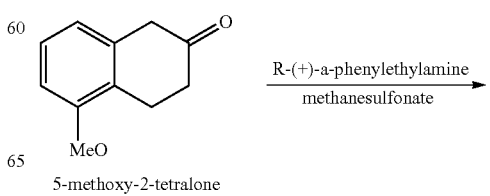

5-methoxy-2-tetralone

-continued

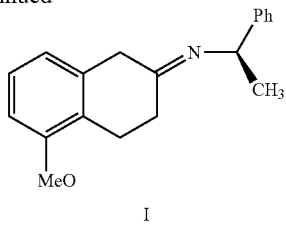

The oily liquid is analyzed by NMR spectroscopy and is determined to have a structural formula consistent to the compound I.

2. Synthesis of Compound II

Add 125 g (409 mMol) of compound I obtained from the above process and 3000 mL tetrahydrofuran into a 2 L four-necked flask; stir until the temperature of the reacting mixture is decreased to reach −20° C.~−15° C.; and then start adding 631 mMol potassium borohydride slowly and allow reaction at −20° C.~−15° C. until the reaction is complete. Adjust pH to about 7 by 10% hydrochloric acid. Concentrate and dry the reactants and then add 500 mL of water and 100 mL ethyl acetate. While stirring, adjust pH to about 10 by 10% sodium hydroxide solution and allow settling. Then the water layer is further extracted by 1500 mL ethyl acetate. Mixing the organic layer obtained from the above two extraction process. Wash twice with 500 mL and 300 mL water respectively. Dry with anhydrous Na$_2$SO$_4$. Filter and concentrate to obtain an oily liquid, which is compound II. The reaction is illustrated as follows:

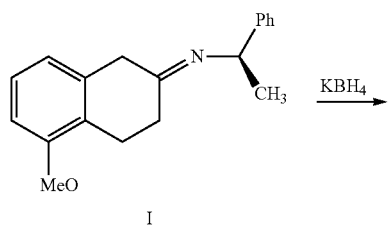

The oily liquid is analyzed by NMR spectroscopy and is determined to have a structural formula consistent to that of the compound II.

3. Synthesis of (S)-2-amino-5-methoxytetralin hydrochloride

Dilute the compound II obtained from the above process with 300 mL ethyl acetate. Then add 500 mL ethyl ether-HCl solution. Obtain a solid by precipitation. Filter and vacuum drying to obtain a generally white solid, which is compound II salt.

Add 100 g (404 mMol) of compound II salt, 2500 mL anhydrous ethanol, 100 mL water and 18 g Pd/C into a 5 L four-necked flask. Introduce nitrogen gas into the flask for 30 minutes. Then, introduce H$_2$ while increasing temperature to 30° C.~35° C. and allow reaction. After the reaction is complete, stop the supply of H$_2$. Filter to obtain a filtrate. Concentrate and dry the filtrate. Add 1500 mL ethyl acetate to the residue, reflux for 30 min, cool and allow crystallization. Filter, dry and vacuum drying to obtain a generally white solid, which is (S)-2-amino-5-methoxytetralin hydrochloride. Based on the quantity of 5-methoxy-2-tetralone, the overall yield is 69.3%, the purity is greater than 99% and the enantiomeric excess is 98.5%. If this generally white solid is further refined once, the refining yield is 91%, the overall yield is 62.5%, the purity is greater than 99.5% and the enantiomeric excess is 99.9%. The reaction is illustrated as follows:

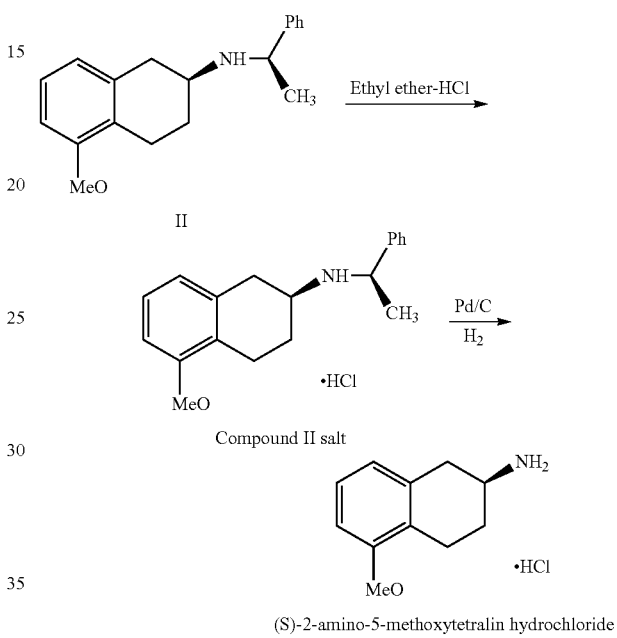

The generally white solid is analyzed by NMR spectroscopy and is determined to have a structural formula consistent to that of the (S)-2-amino-5-methoxytetralin hydrochloride.

Embodiment 3

A Process of Making (S)-2-Amino-5-Methoxytetralin Hydrochloride According to the Preferred Embodiment of the Present Invention 1. Synthesis of Compound I Add 72 g (409 mMol) of 5-methoxy-2-tetralone, 62 g (512 mMol) of R-(+)-a-phenylethylamine, 3.2 g isopropyl titanate and 2000 ml of xylene into a 5 L reaction flask which is opened to manifold; under the protection of nitrogen atmosphere, stir and heat until the reflux reaction is complete. Then concentrate the reaction liquid under vacuum to obtain an oily liquid of compound I. The reaction is illustrated as follows:

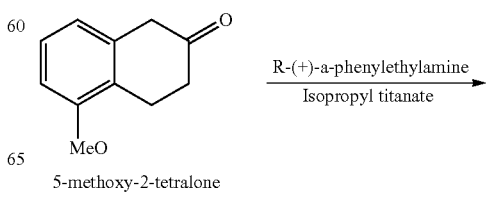

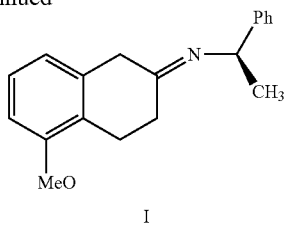

The oily liquid is analyzed by NMR spectroscopy and is determined to have a structural formula consistent to the compound I.

2. Synthesis of Compound II

Add 125 g (409 mMol) of compound I obtained from the above process and 1000 mL anhydrous methanol into a 2 L four-necked flask; stir until the temperature of the reacting mixture is decreased to reach −15° C.~−10° C.; and then start adding 631 mMol lithium borohydride slowly and allow reaction at −15° C.~−10° C. until the reaction is complete. Adjust pH to about 7 by 10% hydrochloric acid. Concentrate and dry the reactants and then add 350 mL of water and 150 mL ethyl acetate. While stirring, adjust pH to about 10 by 10% sodium hydroxide solution and allow settling. Then the water layer is further extracted by 1200 mL ethyl acetate. Mixing the organic layer obtained from the above two extraction process. Wash twice with 350 mL and 200 mL water respectively. Dry with anhydrous $Na_2SO_4$. Filter and concentrate to obtain an oily liquid, which is compound II. The reaction is illustrated as follows:

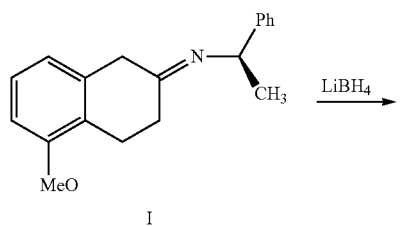

The oily liquid is analyzed by NMR spectroscopy and is determined to have a structural formula consistent to that of the compound II.

3. Synthesis of (S)-2-amino-5-methoxytetralin hydrochloride

Dilute the compound II obtained from the above process with 300 mL ethyl acetate. Then add 500 mL ethyl ether-HCl solution. Obtain a solid by precipitation. Filter and vacuum drying to obtain a generally white solid, which is compound II salt.

Add 100 g (404 mMol) of compound II salt, 2000 mL anhydrous ethanol, 100 mL water and 18 g $Pd(OH)_2/C$ into a 5 L four-necked flask. Introduce nitrogen gas into the flask for 30 minutes. Then, introduce $H_2$ while start increasing temperature to 25° C.~30° C. and allow reaction. After the reaction is complete, stop the supply of $H_2$. Filter to obtain a filtrate. Concentrate and dry the filtrate. Add 1200 mL ethyl acetate to the residue, reflux for 30 min, cool and allow crystallization. Filter, dry and vacuum drying to obtain a generally white solid, which is (S)-2-amino-5-methoxytetralin hydrochloride. Based on the quantity of 5-methoxy-2-tetralone, the overall yield is 67.5%, the purity is greater than 99% and the enantiomeric excess is 98.5%. If this generally white solid is further refined once by ethyl acetate, the refining yield is 93.6%, the overall yield is 64.1%, the purity is greater than 99.5% and the enantiomeric excess is 99.9%. The reaction is illustrated as follows:

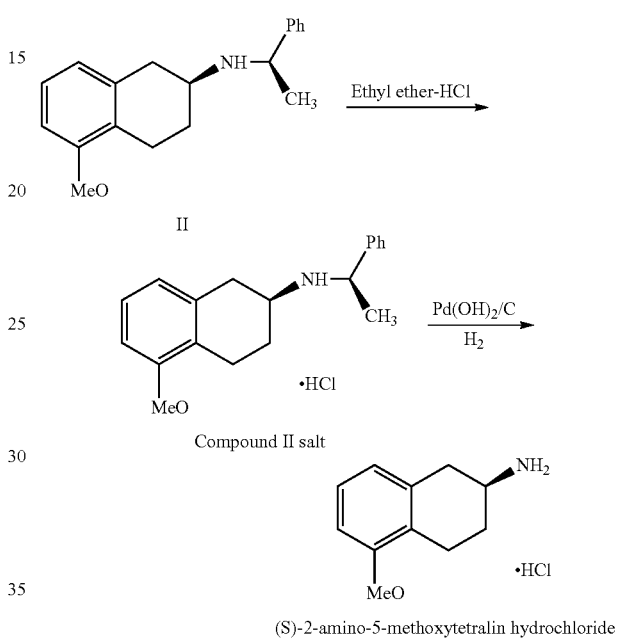

The generally white solid is analyzed by NMR spectroscopy and is determined to have a structural formula consistent to that of the (S)-2-amino-5-methoxytetralin hydrochloride.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of preparing (S)-2-amino-5-methoxytetralin hydrochloride, comprising the steps of:
   (1) producing a compound (I) by addition-elimination reaction of 5-methoxy-2-tetralone and R-(+)-a-phenylethylamine;
   (2) producing a compound (II) by reduction reaction of the compound (I) with a reducing agent; and
   (3) producing a compound (II) hydrochloride by reacting the compound (II) with a salt-forming agent, then carrying out reduction reaction with a palladium-carbon catalyst to produce (S)-2-amino-5-methoxytetralin hydrochloride, where the compound (1) has a structural formula of:

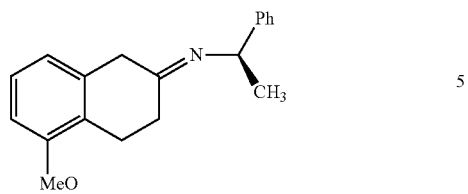

and the compound (II) has a structural formula of:

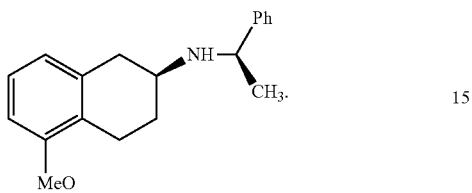

wherein in the step 2, the reducing agent is selected from the group consisting of NaBH$_4$, KBH$_4$, LiBH$_4$ and Zn(BH$_4$)$_2$.

2. The method, as recited in claim 1, wherein in the step 3, the salt-forming agent is ethyl ether HCl or ethyl acetate HCl.

3. The method, as recited in claim 1, wherein in the step 3, the alladium-carbon catalyst is Pd/C or Pd(OH)$_2$/C.

4. The method, as recited in claim 1, wherein in the step 1, a molar ratio of 5-methoxy-2-tetralone and R-(+)-a-phenyl-ethylamine is 1:0.5-5.

5. The method, as recited in claim 1, wherein in the step 2, a molar ratio of the compound (I) and the reducing agent is 1:0.5-5.

\* \* \* \* \*